(12) United States Patent
Hill

(10) Patent No.: US 11,819,394 B1
(45) Date of Patent: Nov. 21, 2023

(54) SANITARY NAPKIN HAVING UNIQUELY SHAPED ABSORBENTS

(71) Applicant: Gretchel Linelia Hill, New York, NY (US)

(72) Inventor: Gretchel Linelia Hill, New York, NY (US)

(73) Assignee: Gretchel Linelia Hill, New York, NY (US)

( * ) Notice: Subject to any disclaimer, the term of this patent is extended or adjusted under 35 U.S.C. 154(b) by 227 days.

(21) Appl. No.: 17/214,808

(22) Filed: Mar. 27, 2021

(51) Int. Cl.
| | |
|---|---|
| *A61F 13/534* | (2006.01) |
| *A61F 13/472* | (2006.01) |
| *A61F 13/511* | (2006.01) |
| *A61F 13/56* | (2006.01) |
| *A61F 13/53* | (2006.01) |

(52) U.S. Cl.
CPC .......... *A61F 13/534* (2013.01); *A61F 13/472* (2013.01); *A61F 13/51104* (2013.01); *A61F 13/5616* (2013.01); *A61F 2013/530481* (2013.01)

(58) Field of Classification Search
CPC .................. A61F 13/534; A61F 13/472; A61F 13/51104; A61F 13/5616; A61F 2013/530481
See application file for complete search history.

(56) References Cited

U.S. PATENT DOCUMENTS

| | | | | | |
|---|---|---|---|---|---|
| 5,057,096 | A | * | 10/1991 | Faglione | A61F 13/47227 604/385.17 |
| 8,870,842 | B2 | * | 10/2014 | Hill | A61F 13/47227 604/385.17 |
| 2004/0254554 | A1 | * | 12/2004 | Mavinkurve | A61F 13/51104 604/380 |
| 2005/0267434 | A1 | * | 12/2005 | Tanio | A61F 13/4702 604/385.01 |
| 2021/0045943 | A1 | * | 2/2021 | Blasius | A61F 13/8405 |

* cited by examiner

*Primary Examiner* — Daniel J Colilla

(57) ABSTRACT

A sanitary napkin is disclosed having a body-facing surface and a garment-facing surface. The sanitary napkin also has a first end, a second end, and a pair of sides. The sanitary napkin has a longitudinal central axis, a transverse central axis, a main absorbent, and first and second 3-dimensional absorbent members. The main absorbent, and the first and second 3-dimensional absorbent members are joined together between a liquid pervious top sheet and a liquid-impervious back sheet. All three absorbents contain superabsorbent. The sanitary napkin also has a pair of wings extending outward from the sides of the sanitary napkin and has garment adhesive on the garment facing surfaces to secure the sanitary napkin and the pair of wings to the crotch portion of an undergarment. This sanitary napkin is designed to absorb heavy to excessive menstrual fluid flow.

10 Claims, 2 Drawing Sheets

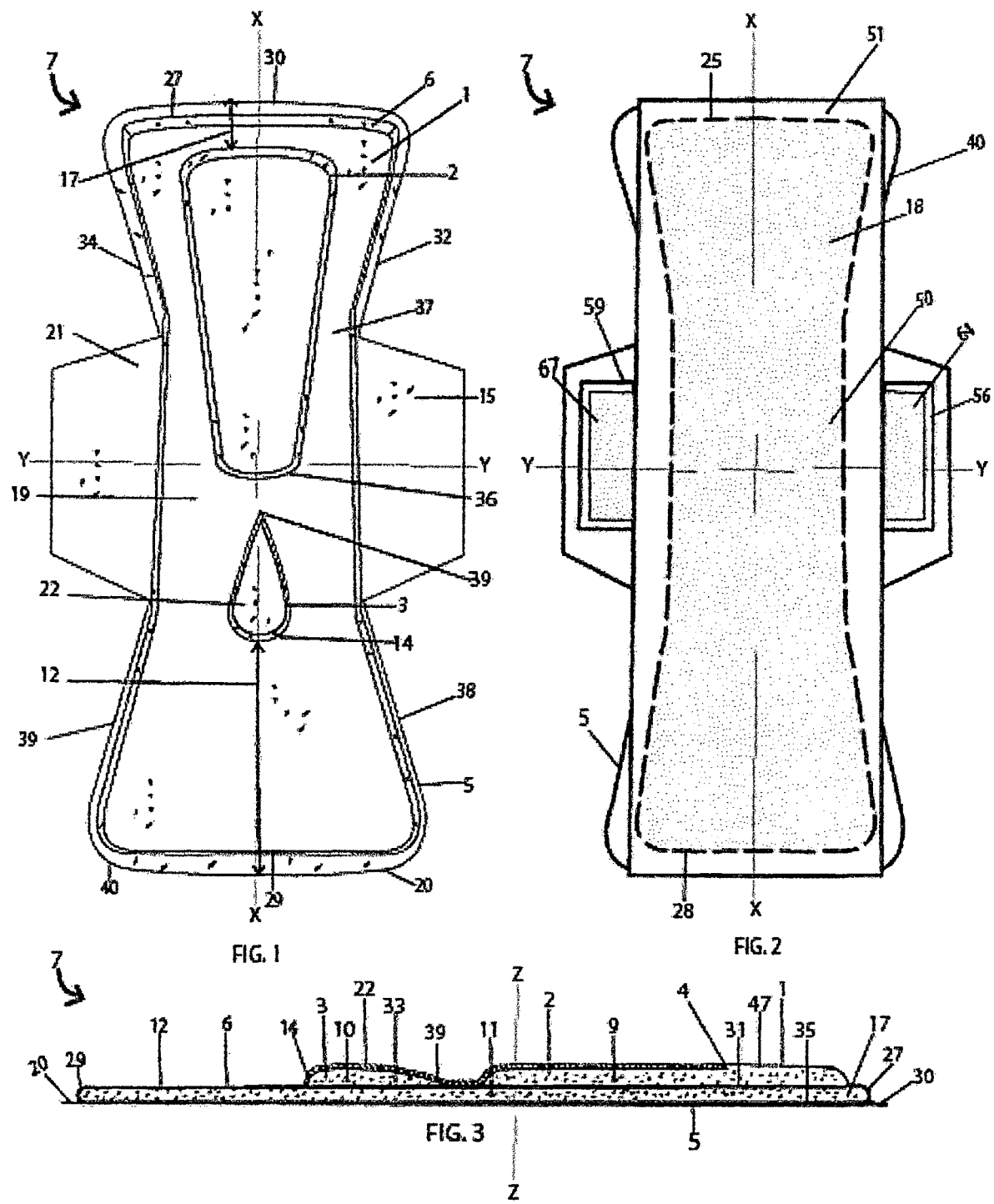

SANITARY NAPKIN HAVING UNIQUELY SHAPED ABSORBENTS

FIELD OF THE INVENTION

The present invention relates to a sanitary napkin having first and second 3-dimensional absorbent members joined to the main absorbent and sealed between a liquid pervious top sheet and a liquid-impervious back sheet. The first and second 3-dimensional absorbent members function as back up protection to the main absorbent for handling heavy and extreme menstrual fluid flow.

BACKGROUND OF THE INVENTION

Absorbent articles, such as sanitary napkins, panty liners, disposable diapers, incontinence products, and bandages are designed to absorb and retain menstrual fluid, body fluid and other discharges from a human body. The absorbent articles can also prevent soiling of the adjacent clothing. But due to fibroids, endometrioses, postpartum and other reasons, some women experience a heavy and excessive menstrual fluid discharge. For this reason, a sanitary napkin is needed which will provide comfort, provide psychological security, is discreet, and can provide quick absorbent take-up and provide extra protection.

Women who have a monthly menstrual fluid flow of about 80 ml or more falls are classified as having heavy menstrual bleeding. Such heavy menstrual bleeding could interfere with a woman's normal day-to-day activity. Heavy menstrual bleeding can prompt some women to wear double sanitary napkins, pull-ups, diapers, or an overnight sanitary napkin along with a tampon for extra protection. It is estimated that about thirty percent (30%) of the women in the USA occasionally suffer from heavy menstrual bleeding. Extra protection is especially needed when such a woman sits down because a heavy menstrual fluid gush from the vagina could occur which may include large clots and thick tissue. The pressure exerted on the body during sitting can cause the menstrual fluid to flow rearward towards the rear of the sanitary napkin and between the buttocks. This menstrual fluid could reach as far as the top rim of her panties, causing an uncomfortable wet feeling and possibly soiling her undergarment and/or outerwear. Such an event could leave a woman feeling psychologically insecure and embarrassed.

Some women, who suffer from heavy menstrual bleeding, are advised to have surgery, such as to remove uterine fibroids or to have a hysterectomy. During childbearing years, many women elect to forego major surgery, especially a hysterectomy. Some women who suffer from heavy menstrual bleeding deal with their problem by protecting themselves by using different sanitary products so as to live another day until childbearing ends. Some women elect to use a sanitary pad, which provides added protection. For example, U.S. Pat. No. 8,870,842 issued to Gretchel Linelia Hill on Oct. 28, 2014, describes a sanitary pad with a longitudinal rear raise uplift target zone absorbent core that extends to the back lateral end. The raise uplift absorbent core is a section in the rear of the sanitary pad, which can absorb gushing menstrual fluid to prevent wetness to the backside. But even this product may not satisfy the needs of some women.

Now, a sanitary napkin has been invented with improved menstrual fluid handling such that heavy, excessive and gush menstrual fluid flow is absorbed rapidly and remains in the sanitary napkin. This means that less menstrual fluid contacts the skin of the woman and the undergarment.

SUMMARY OF THE PRESENT INVENTION

Briefly, this invention relates to a sanitary napkin, which can handle a heavy menstrual fluid flow.

The sanitary napkin has a body-facing surface, a garment-facing surface, a first end, a second end, and a pair of sides. The sanitary napkin has a longitudinal central axis and a transverse central axis. The sanitary napkin includes a liquid pervious top sheet having a body-facing surface and a liquid-impermeable back sheet having a garment-facing surface. A main absorbent is positioned between the top sheet and the back sheet. The main absorbent contains a superabsorbent and has a top surface. The sanitary napkin also has a first 3-dimensional absorbent member secured to the top surface of the main absorbent and is aligned along the longitudinal central axis and is located between the first end of the sanitary napkin and the transverse central axis. The first 3-dimensional absorbent member contains a superabsorbent. The sanitary napkin further includes a second 3-dimensional absorbent member secured to the top surface of the main absorbent and is aligned along the longitudinal central axis and is located between the transverse central axis and the second end. The second 3-dimensional absorbent member also contains a superabsorbent. The sanitary napkin further includes a pair of wings extending outward from the pair of sides of the sanitary napkin. Each of the pair of wings is bifurcated by the transverse central axis, and each of the pair of wings has a lower surface. A first garment adhesive is secured to the garment-facing surface of the sanitary napkin. The first garment adhesive releasable attaches the sanitary napkin to an interior surface of a crotch portion of an undergarment. Lastly, the sanitary napkin includes two strips of garment adhesive. Each strip of garment adhesive is secured to one of the lower surfaces of each of the pair of wings. The two strips of garment adhesive attach to an exterior surface of a crotch portion of the undergarment after each of the pair of wings are folded around the sides of the crotch portion of the undergarment to retain the sanitary napkin adjacent to a user's perineum.

In another embodiment, the sanitary napkin has a body-facing surface, a garment-facing surface, a first end, a second end, and a pair of sides. The sanitary napkin also has a longitudinal central axis and a transverse central axis. The sanitary napkin includes a liquid pervious top sheet having a body-facing surface and a liquid-impermeable back sheet having a garment-facing surface. A main absorbent is positioned between the top sheet and the back sheet. The main absorbent contains a superabsorbent, and the main absorbent has a top surface. The sanitary napkin also includes a first 3-dimensional absorbent member secured to the top surface of the main absorbent and is aligned along the longitudinal central axis and is located between the first end of the sanitary napkin and the transverse central axis. The first 3-dimensional absorbent member has a length, a width and a height. The sanitary napkin also includes a second 3-dimensional absorbent member, which is secured to the top surface of the main absorbent and is aligned along the longitudinal central axis and is located between the transverse central axis and the second end. The second 3-dimensional absorbent member has a length, a width and a height. The length and width of the second 3-dimensional absorbent member is less than the length and width of the second 3-dimensional absorbent member. The height of the second 3-dimensional absorbent member is equal to the height of the first 3-dimensional absorbent member. The sanitary napkin also includes a pair of wings extending outward from the pair of sides of the sanitary napkin. Each of the pair of wings is bifurcated by the transverse central axis, and each of the pair of wings has a lower surface. The sanitary napkin also includes a first garment adhesive secured to the garment facing surface of the sanitary napkin. The first garment adhesive releasably attaches the sanitary napkin to an interior surface of a crotch portion of an undergarment. The sanitary napkin further includes two strips of garment adhesive. Each strip of garment adhesive is secured to one of the lower surfaces of each of the pair of wings. The two strips of garment adhesive attach to an exterior surface of a crotch portion of the undergarment after each of the pair of wings is folded around the sides of the crotch portion of the undergarment to retain the sanitary napkin adjacent to a user's perineum. Lastly, removable peel strips cover the first garment adhesive and the two strips of garment adhesive to prevent the garment adhesive from becoming contaminated prior to attachment to an undergarment. In still another embodiment, the sanitary napkin has a body-facing surface, a garment-facing surface, a front end, a rear end, and a pair of sides. The sanitary napkin has a longitudinal central axis and a transverse central axis. The sanitary napkin includes a liquid pervious top sheet having a body-facing surface and a liquid-impermeable back sheet having a garment-facing surface. The sanitary napkin also has a main absorbent positioned between the top sheet and the back sheet. The main absorbent containing a superabsorbent has a top surface. The sanitary napkin also includes a first 3-dimensional absorbent member positioned on the top surface of the main absorbent and is aligned along the longitudinal central axis and is located between the front end of the sanitary napkin and the transverse central axis. The first 3-dimensional absorbent member contains a superabsorbent. The sanitary napkin also includes a second 3-dimensional absorbent member positioned on the top surface of the main absorbent and is aligned along the longitudinal central axis and is located between the transverse central axis and the rear end. The second 3-dimensional absorbent member contains a superabsorbent. The sanitary napkin further includes a pair of wings extending outward from the pair of the sides of the sanitary napkin. Each of the pair of wings is bifurcated by the transverse central axis, and each of the pair of wings has a lower surface. The sanitary napkin also includes a first garment adhesive secured to the garment-facing surface of the sanitary napkin. The first garment adhesive releasably attaches the sanitary napkin to an interior surface of a crotch portion of an undergarment. The sanitary napkin also includes two strips of garment adhesive. Each strip of garment adhesive is secured to one of the lower surfaces of each of the pair of wings. The two strips of garment adhesive attach to an exterior surface of a crotch portion of the undergarment after each of the pair of wings is folded around sides of the crotch portion of the undergarment to retain the sanitary napkin adjacent to a user's perineum. Lastly, the sanitary napkin includes removable peel strips covering the first garment adhesive and the two strips of garment adhesive to prevent the garment adhesive from becoming contaminated prior to attachment to an undergarment. The general object of this invention is to provide a sanitary napkin having uniquely shaped absorbents for handling heavy menstrual fluid flow. A more specific object of this invention is to provide a sanitary napkin having a main absorbent core and first and second 3-dimensional absorbents members joined thereto to handle heavy menstrual fluid flow.

Another object of this invention is to provide a sanitary napkin, which is discreet and comfortable to wear.

Still another object of this invention is to provide a sanitary napkin that exhibits improved body fit relative to a woman's body.

Still further, an object of this invention is to provide a sanitary napkin, which can be reasonably manufactured.

Other objects and advantages of the present invention will become more apparent to those skilled in the art in view of the following description and the accompanying drawings.

BRIEF DESCRIPTION OF THE DRAWING

The present invention will be understood fully from the detailed description in conjunction with the drawings, in which:

FIG. 1 is a top view of a sanitary napkin.

FIG. 2 is a bottom view thereof of the sanitary napkin shown in FIG. 1.

FIG. 3 is a side view of the sanitary napkin shown in FIG. 1.

DETAILED DESCRIPTIONS OF THE INVENTION

Figure 4:
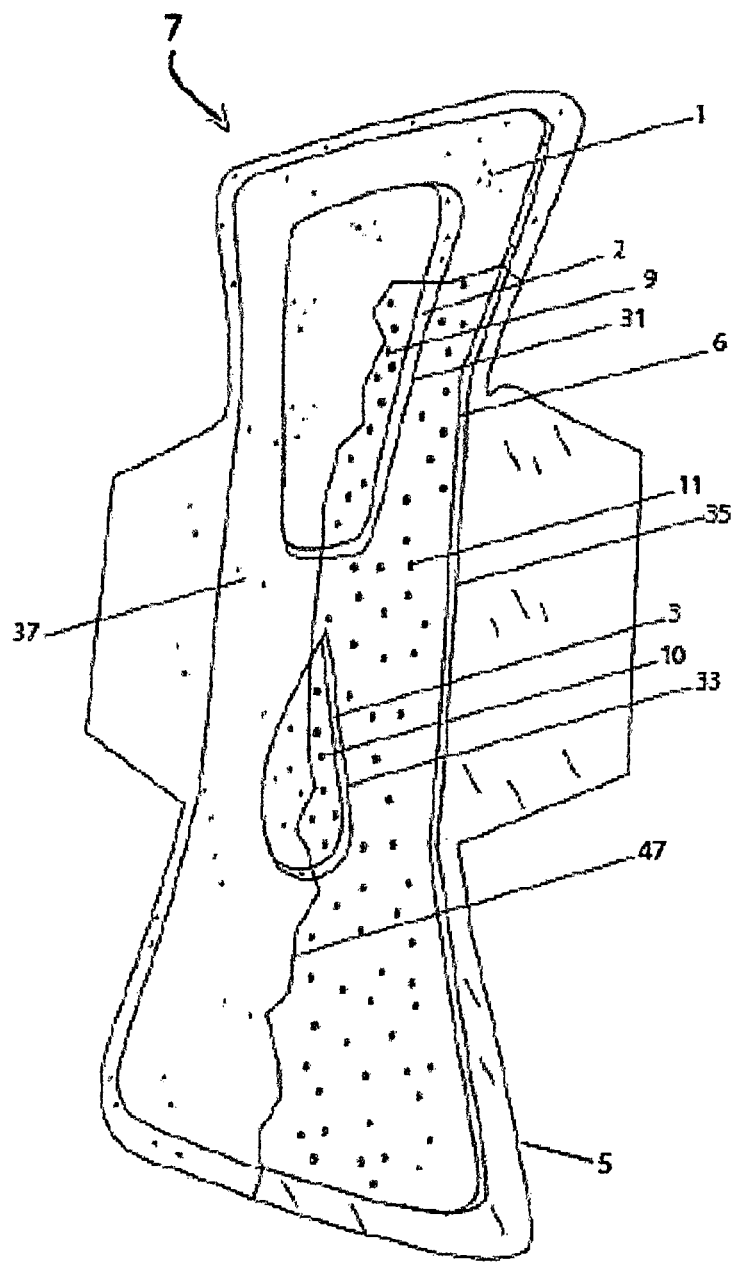
FIG. 4 is an isometric view of a sanitary napkin shown in FIG. 1, with parts broken away to reveal the internal components.

Referring to FIGS. 1-3, a sanitary napkin 7 is shown having a body-facing surface 37, a garment-facing surface 40, a first end 30 and a second end 20. The sanitary napkin 7 has a longitudinal central axis X—X, a transverse central axis Y—Y, and a vertical central axis Z—Z. The sanitary napkin 7 also has a main absorbent 6, which has a first end 27 and a second end 29. The first and second ends, 27 and 29 respectively, can be aligned parallel to one another. The main absorbent 6 contains a superabsorbent 11. The superabsorbent 11 can vary in size, quantity shape, distribution, etc. The sanitary napkin 7 can vary in length. The sanitary napkin 7 can have a length of about 256 mm measured between the first and second ends, 27 and 29 respectively. The sanitary napkin 7 has a width that can vary in dimension. The width of the sanitary napkin 7 can be about 114 mm and can tapers down to a center location 19 of about 76 mm. The sanitary napkin 7 also has sides 32 and 34 located adjacent to a first end 30, and sides 38 and 39 located adjacent to a second end 20. The sanitary napkin 7 further includes a liquid pervious top sheet 1 and liquid-impervious back sheet 5. The liquid pervious top sheet 1 is aligned opposite to the liquid-impervious back sheet 5.

The liquid pervious top sheet 1 may be a relatively low density, bulky, high-loft nonwoven web material. The liquid pervious top sheet 1 may be composed of different fibers, such as perforated, double or triple perforated, nonwoven or polyester, or polypropylene, or it may include a mixture of more than one raw material. The liquid pervious top sheet 1 may be composed of bi-component or conjugate fibers having a low melting point component and a high melting point component. The material can be from various natural, organic, biodegradable, and synthetic materials such as nylon, polyester, rayon (combined with other fibers), cotton, acrylic material, cloth fabric materials and the like and combinations. Desirably, the liquid-permeable cover layer 1 has a basis weight in the range of about 10 grams per square meter (gsm) to about 75 gsm. The liquid pervious top sheet 1 can have a relatively high degree of wettability; therefore, the liquid-permeable cover layer 1 contributes little to the time taken for the sanitary napkin 7 to absorb a given quantity of menstrual fluid as well as other body fluids (penetration time). The fibers of the liquid pervious top sheet 1 should not lose their physical properties when they are wetted; in other words, they should not collapse or lose their resiliency when subjected to water or body liquid. The liquid pervious top sheet 1 also functions to transfer the liquid quickly to the underlying layers of the sanitary napkin 7. Thus, the liquid pervious top sheet 1 is advantageously wettable, hydrophilic, and porous.

The liquid-impervious back sheet 5 prevents body fluid trapped in the main absorbent 6, and in the first and second 3-dimensional absorbent members, 2 and 3 respectively, from egressing the sanitary napkin 7 and staining the wearer's undergarment. The liquid-impervious back sheet 5 can be constructed from various materials. Typically, the liquid-impervious back sheet 5 is made from a polymer film. Desirably, the liquid-impervious back sheet 5 has a basis weight which ranges from between about 14 gsm to about 19 gsm. The liquid-impervious back sheet 5 may be breathable, for example, permitting vapors to pass there through. The liquid-impervious back sheet 5 can be constructed from non-woven materials. The liquid-impervious back sheet 5 can also be constructed from micro-porous films in which micro porosity is created by, among other things, stretching an oriented film. The liquid-impervious back sheet 5 can be formed from one, two or multiple layers of porous films, melt-blown materials, or combinations thereof. The liquid-impervious back sheet 5 can function to provide a tortuous path whose surface characteristics provide a liquid surface repellent. The liquid pervious top sheet 1 and the liquid-impervious back sheet 5 are desirably joined together along their marginal portions to form an enclosure or flange seal that maintains the main absorbent 6, and the first and second 3-dimensional absorbent members, 2 and 3 respectively, captive. The various layers 1, 2, 3, 4 and 5 can be secured or joined together by an adhesive, by heat bonding, by ultrasonic bonding, by radio frequency sealing, by mechanical crimping, stitching, and the like or by a combination of the above.

The width of the sanitary napkin 7 can vary. The width of the sanitary napkin 7 can range from between about 127 mm to about 145 mm. The main absorbent 6 has a height, which can vary. The height is measured along the vertical central axis Z—Z. The height of the main absorbent 6 can be less than about 9.0 mm. Desirably, the height of the main absorbent 6 is less than about 8.5 mm. More desirably, the height of the main absorbent 6 is less than 8.0 mm.

The first 3-dimensional absorbent member 2 can vary in size and configuration. The first 3-dimensional absorbent member 2 can have a quadrilateral shape; a trapezoid shape or any other desired geometrical shape. The first 3-dimensional absorbent member 2 contains a superabsorbent 9. The superabsorbent 9 can vary in size, quantity shape, distribution, etc. The first 3-dimensional absorbent member 2 has a first end 17 and a second end 36. The first 3-dimensional absorbent member 2 has a height, which can vary. The height of the first 3-dimensional absorbent member 2 is measured along the vertical central axis Z—Z. The height of the first 3-dimensional absorbent member 2 can be less than, equal to, or be greater than the height of the main absorbent 6. The height of the first 3-dimensional absorbent member 2 can range from between about 3 mm to about 15 mm. Desirably, the height of the first 3-dimensional absorbent member 2 is less than about 12 mm. More desirably, the height of the first 3-dimensional absorbent member 2 is less than about 10 mm. Even more desirably, the height of the first 3-dimensional absorbent member 2 is less than about 9 mm. Most desirably, the height of the first 3-dimensional absorbent member 2 is less than about 8.5 mm. Most desirably, the height of the first 3-dimensional absorbent member 2 is less than about 8 mm.

The first 3-dimensional absorbent member 2 has a length-measured parallel to the longitudinal central axis X—X. The length of the first 3-dimensional absorbent member 2 can vary.

The first 3-dimensional absorbent member 2 is joined to the body-facing surface 37 of the main absorbent 6. The first end 17 of the first 3-dimensional absorbent member 2 has a greater dimension than the second end 36. The first end 17 is located adjacent to the first end 30 of the sanitary napkin 7 while the second end 36 is located approximate the central location 19. The first and second ends, 17 and 36 respectively, of the first 3-dimensional absorbent member 2 can have an arcuate shape. Alternatively, the first and second ends, 17 and 36 respectively, can be linear or have some other desired shape.

The first and second ends, 30 and 20 respectively, of the sanitary napkin 7 are aligned parallel to one another. Likewise, the first and second ends, 17 and 36 of the first 3-dimensional absorbent member 2 are aligned parallel to one another.

The second 3-dimensional absorbent member 3 can vary in size and configuration. The second 3-dimensional absorbent member 3 is shown having a pear shape with an apex 41. The apex 41 is positioned adjacent to the transverse central axis Y—Y. The second 3-dimensional absorbent member 3 is smaller than the first 3-dimensional absorbent member 2. The second 3-dimensional absorbent member 3 contains a superabsorbent 10. The superabsorbent 10 can vary in size, quantity shape, distribution, etc. The second 3-dimensional absorbent member 3 has a height, which can vary. The height of the second 3-dimensional absorbent member 3 can be less than, equal to, or be greater than the height of the main absorbent 6. The height of the second 3-dimensional absorbent member 3 can range from between about 3 mm to about 15 mm. Desirably, the height of the second 3-dimensional absorbent member 3 is less than about 12 mm. More desirably, the height of the second 3-dimensional absorbent member 3 is less than about 10 mm. Even more desirably, the height of the second 3-dimensional absorbent member 3 is less than about 9 mm. Most desirably, the height of the second 3-dimensional absorbent member 3 is less than about 8.5 mm. Most desirably, the height of the second 3-dimensional absorbent member 3 is less than about 8 mm.

The height of the second 3-dimensional absorbent member 3 can be less than, equal to, or be greater than the height of the first 3-dimensional absorbent member 2. Desirably, the height of the second 3-dimensional absorbent member 3 is equal to the height of the first 3-dimensional absorbent member 2. The second 3-dimensional absorbent member 3 is joined to the body-facing surface 37 of the main absorbent 6. The first and second 3-dimensional absorbent members, 2 and 3 respectively, can have the same thickness or each can have a different thickness. Each of the first and second 3-dimensional absorbent members, 2 and 3 respectively, can have a thickness of from between about 4 mm to about 6 mm. Desirably, each of the first and second 3-dimensional absorbent members, 2 and 3 respectively, can have the thickness of greater than about 6.5 mm.

The second 3-dimensional absorbent member 3 has a length-measured parallel to the longitudinal central axis X—X. The length of the second 3-dimensional absorbent member 3 can vary. The length of the first 3-dimensional absorbent member 2 is at least about twice the length of the second 3-dimensional absorbent member 3. Desirably, the length of the first 3-dimensional absorbent member 2 is at least about 2.5 times the length of the second 3-dimensional absorbent member 3.

Referring now to FIG. 4, the main absorbent 6, the first 3-dimensional absorbent member 2, and the second 3-dimensional absorbent member 3 can each be composed of fibrous materials, such as thermally bonded air-laid, wood pulp, polyester, rayon, flexible foam, fabrics or the like, or combinations thereof. The main absorbent 6 contains a superabsorbent 11. The first 3-dimensional absorbent member 2 contains a superabsorbent 9 and the second 3-dimensional absorbent member 3 contains a superabsorbent 10. The kind, size and type of superabsorbent 9, 10 and 11 contained in the three different absorbents 6, 2 and 3 can vary. In addition, the superabsorbent 9, 10 and 11 can be spaced out within each absorbent 6, 2 and 3 such that a higher amount of the superabsorbent may be located towards the lower surface of each absorbent than is located near the upper surface of each layer.

The main absorbent 6, the first 3-dimensional absorbent member 2, and the second 3-dimensional absorbent member 3 are secured or joined together for effective liquid distribution. The three absorbent layers 6, 2 and 3 can be joined or secured together by various means known to those skilled in the art. For example, the first 3-dimensional absorbent member 2 and the second 3-dimensional absorbent member 3 can be positioned adjacent to one another, can be pressed together, can be attached with an adhesive, etc. In another example, the main absorbent 6, the first 3-dimensional absorbent member 2, and the second 3-dimensional absorbent member 3 are secured or joined together by being enclosed by the liquid pervious top sheet 1 (or by a transfer layer 4 if such a layer is present) and the underlying liquid-impervious back sheet 5.

The main absorbent 6, the first 3-dimensional absorbent member 2, and the second 3-dimensional absorbent member 3 can each have a basis weight in the range of about 70 gsm to about 600 gsm. The main absorbent 6, the first 3-dimensional absorbent member 2, and the second 3-dimensional absorbent member 3 should also contain a superabsorbent 9, 10 and 11, as explained above. Superabsorbent are materials, which are capable of absorbing and retaining at least about ten times their weight in body fluid. The superabsorbents 9, 10 and 11 can vary in size and shape. The superabsorbents 9, 10 and 11 can be particles or flaks of inorganic or organic cross-linked hydrophilic polymers. Furthermore, the superabsorbents 9, 10 and 11 can be in the form of powder, grains, granules, sheets, or fibers.

The sanitary napkin 7 can also optionally include a transfer layer 4. The transfer layer 4 is positioned above the main absorbent 6, and the first and second 3-dimensional absorbent members, 2 and 3 respectively. The transfer layer 4 can also be positioned underneath the first and second 3-dimensional absorbent members, 2 and 3 and on top of the main absorbent 6. The transfer layer 4 can also extend over at least a portion of the main absorbent 6. The transfer layer 4 usually extends over that portion of the main absorbent 6 which is located between the first and second 3-dimensional absorbent members, 2 and 3 respectively. The length of the transfer layer 4 can vary. The transfer layer 4 can have a length which extends from the second end 14 of the second 3-dimensional absorbent member 3 toward the first end 17 of the first 3-dimensional absorbent member. The transfer layer 4 does not have to extend completely to the first end 17 of the first 3-dimensional absorbent member. The transfer layer 4 could extend over a portion of the main absorbent 6 located rearward of the second 3-dimensional absorbent member 3, or over the entire main absorbent 6, if desired. The transfer layer 4 is located beneath the liquid pervious top sheet 1. The transfer layer can be secured or joined to the liquid pervious top sheet 1 or merely be positioned beneath the liquid pervious top sheet 1. Likewise, the transfer layer 4 can be secured or joined to the first and second 3-dimensional absorbent members, 2 and 3 respectively, or merely be positioned above the first and second 3-dimensional absorbent members, 2 and 3 respectively. Typically, the transfer layer 4 is simply positioned below the liquid pervious top sheet 1 and above the first and second 3-dimensional absorbent members, 2 and 3 respectively.

The transfer layer 4 functions to receive body fluid (menstrual fluid) from the liquid pervious top sheet 1 and distribute it over a greater surface area to the underlying first and second 3-dimensional absorbent members, 2 and 3 respectively. The transfer layer 4 can also distribute the body fluid to the main absorbent 6 when it extends over at least a portion of the main absorbent 6. The transfer layer 4 is usually denser and has a larger proportion of smaller pores than the liquid pervious top sheet 1. This structure helps to distribute the body fluid to the first and second 3-dimensional absorbent members, 2 and 3 respectively. The characteristics and structure of the transfer layer 4 enable it to temporarily retain and distribute the body fluid. The transfer layer 4 will actually pull the body fluid away from the body side surface 37 of the liquid pervious top sheet 1 and transfer the body fluid to the first and second 3-dimensional absorbents, 2 and 3 respectively. This action by the transfer layer 4 thereby prevents the body fluid from rewetting the liquid pervious top sheet 1 and its body-facing surface 37. However, the transfer layer 4 should not be so dense as to prevent the passage of body fluid through the transfer layer 4 and into the underlying absorbents 2, 3, and 6. The transfer layer 4 can have a basis weight ranging from between about 30 gsm to about 70 gsm. Sometimes the transfer layer 4 is referred to as a fluid acquisition layer.

Referring to FIG. 3, the first 3-dimensional absorbent member 2 has a length that can vary. The transfer layer 4 can extend across at least about fifty percent (50%) of the length of the first 3-dimensional absorbent member 2. Desirably, the transfer layer 4 can extend across at least about sixty percent (60%) of the length of the first 3-dimensional absorbent member 2. The second 3-dimensional absorbent member 3 also has a length. The transfer layer 4 can extend across at least about ninety percent (90%) of the length of the second 3-dimensional absorbent member 3. Desirably, the transfer layer 4 extends across the entire length of the second 3-dimensional absorbent member 3.

Referring to FIGS. 1 and 2, the sanitary napkin 7 has a pair of wings 15 and 21 extending outward from the pair of sides 32 and 34, and 38 and 39 of the sanitary napkin 7. The pair of wings 15 and 21 can vary in size, shape and configuration. Desirably, each of the pair of wings 15 and 21 are identical in size and shape. Each of the pair of wings 15 and 21 is bifurcated by the transverse central axis Y—Y. Each of the pair of wings 15 and 21 has a lower surface 42. At the transverse central axis Y—Y, the distance between the outer edges of the pair of wings 15 and 21 can range from between about 153 mm to about 178 mm.

The main absorbent 6, and the first and second 3-dimensional absorbent members, 2 and 3 respectively, are enclosed and joined together within a liquid pervious top sheet 1 and a liquid-impervious back sheet 5. The first 3-dimensional absorbent member 2 can vary in size and shape. The length from the first end 17 of the first 3-dimensional absorbent member 2 to the first end 30 of the sanitary pad 7 can vary. Typically, this distance is about 35 mm. The first 3-dimensional absorbent member 2 has a length ranging from between about 92 mm to about 100 mm. The width of the first end 17 of the first 3-dimensional absorbent member 2 is about 51 mm. The width of the first 3-dimensional absorbent member 2 can narrow down to a middle point 59 where it will have a width of about 41 mm. The width of the first 3-dimensional absorbent member 2 can continue to narrow down to the second end 36 where it will have a width of about 24 mm.

The second 3-dimensional absorbent member 3 can also vary in size and shape. The length of the second 3-dimensional absorbent member 3 is about 52 mm. The width of the second end 14 of the second 3-dimensional absorbent member 3 is about 26 mm. The width of the second end 14 of the second 3-dimensional absorbent member 3 can narrow down to a middle point 45 of about 22 mm. The width of the second 3-dimensional absorbent member 3 can continue to narrow down to the second end 41 where it forms an apex. At the apex, the width of the second 3-dimensional absorbent member 2 can be about 17 mm or less.

Referring again to FIGS. 1 and 4, the second 3-dimensional absorbent member 3 has a pear shape with an apex at end 41. The apex is positioned adjacent to the transverse central axis Y—Y.

The overall length of the sanitary pad 7 can range from between about 230 mm to about 356 mm. The length of the second 3-dimensional member absorbent 3, measured along the longitudinal central axis X—X can vary. The distance from the second end 14 of the second 3-dimensional member absorbent 3 to the second end 20 of the sanitary napkin 7 can range from between about 73 mm to about 104 mm.

It should be understood that construction adhesive could be used to join the various layers 1, 2, 3, 4 and 5 of the sanitary napkin 7. The construction adhesive is not shown in the drawings. The various layers 1, 2, 3, 4 and 5 of the sanitary napkin 7 can be joined together using different methods, including but not limited to: thermal bonding, adhesive bonding, ultrasonic bonding, glue bonding, etc. The basis weight of the construction adhesive can range from between about 10 gsm to about 25 gsm.

It should also be understood that the sanitary napkin 7 could be manufactured by hand or by using sanitary napkin machines, which are known to those skilled in the art. In addition, conventional materials can be used to construct the sanitary napkin 7. All of the materials needed to construct the sanitary napkin are commercially available in the United States.

Still referring to FIG. 2, a first garment adhesive 18 is secured to the garment-facing surface 40 of the sanitary napkin 7. The first-garment adhesive 18 releasably attaches the sanitary napkin 7 to an interior surface of a crotch portion of an undergarment (not shown). A strip of garment adhesive 64 is secured to the lower surface 42 of one of the pair of wings 15 and 21, and a second strip of garment adhesive 67 is secured to the lower surface 42 of the other of the pair of wings 15 and 21. The two strips of garment adhesive 64 and 67 are designed to adhere to an exterior surface of a crotch portion of an undergarment after each of the pair of wings 15 and 21 is folded to the sides of the crotch portion of the undergarment. The first garment adhesive 18 and the two strips of garment adhesives, 64 and 67, will retain the sanitary napkin 7 adjacent to a user's perineum. The first garment adhesive 18 can vary in length.

The length of the first garment adhesive 18 is measured parallel to the longitudinal central axis X—X. The length of the first garment adhesive 18 can range from between about 190 mm to about 253 mm. The width of the first garment adhesive 18 can vary. The width of the first garment adhesive 18 can narrow down towards a center point 50 to about 63 millimeters (mm). The width of the first garment adhesive 18 at a first end 25 and at a second end 28 can range from between about 76 mm to about 102 mm.

The first garment adhesive 18 is secured to a garment-facing surface 40 of the sanitary napkin 7. The first garment adhesive 18 releasably attaches the sanitary napkin 7 to an interior surface of a crotch portion of an undergarment (not shown). A removable release paper 51 can cover the first garment adhesive 18. Two additional strips of release paper 51, 51 can cover the garment adhesives, 64 and 67, positioned on the lower surfaces 42, 42 of the pair of wings 15 and 21. The basis weight of each of the garment adhesives 18, 64 and 67 can vary. Desirably, the basis weight of the garment adhesives 18, 64 and 67 will range from between about 10 gsm to about 25 gsm.

Still referring to FIG. 2, a release paper or removable peel strip 51 covers the first garment adhesive 18. Sometimes the release paper 51 is referred to as a "removable peel strip". Two additional strips of release paper (removable peel strips) 51, 51 can cover the two strips of garment adhesives, 64 and 67. All three pieces of release paper (peel strips) 51, 51 and 51 will be removed prior to placing the sanitary napkin 7 in the crotch portion of an undergarment. The release paper (removable peel strip) 51 serves to keep the garment adhesive 18, 64 and 67 free from contamination.

Referring again to FIG. 3, the transfer layer 4 is positioned below the liquid pervious top sheet 1. The transfer layer 4 can be joined or secured to the liquid pervious top sheet 1 by a bond 47. The bond 47 can be an adhesive bond, glue, a co-adhesive, a thermal bond, a chemical bond, etc. The transfer layer 4 is positioned on top of a portion of the main absorbent 6 and above the first and second 3-dimensional absorbents members, 2 and 3 respectively. The transfer layer 4 can completely cover the second 3-dimensional absorbent member 3, if desired.

The first and second 3-dimensional absorbent member, 2 and 3 respectively, have a length and a height, as taught above. The first 3-dimensional absorbent member 2 is at least about twice the length of the second 3-dimensional absorbent member 3. The length of the second 3-dimensional absorbent member 3 is shorter than the first 3-dimensional absorbent member 2. The height of the first 3-dimensional absorbent member 2 can be equal to the height of the second 3-dimensional absorbent member 3. The first and second 3-dimensional absorbent members, 2 and 3 respectively, are positioned and can be secured to the top of the main absorbent 6 by bonds 31 and 33. The bond, 31 and 33 can be an adhesive bond, glue, a co-adhesive, a thermal bond, a chemical bond, etc. The main absorbent 6 is joined or secured to the liquid-impervious back sheet 5 by a bond 35. The bond 35 can be an adhesive, glue, a co-adhesive, a thermal bond, a chemical bond, etc. The bonds 31, 33 and 35 keep the various layers 2, 3, 4, 5 and 6 together.

Referring to FIGS. 3 and 4, the sanitary pad 7 has a pair of wings 15 and 21. The sanitary napkin 7 also has a body-facing surface 37, a main absorbent 6, a first 3-dimensional absorbent member 2 and a second 3-dimensional absorbent member 3. The first 3-dimensional absorbent member 2 has a quadrilateral shape and is joined or secured by the bond 31 on top of the main absorbent 6. The second 3-dimensional absorbent member 3 has a pear shape and is joined or secured by the bond 33 on top of the main absorbent 6. The main absorbent 6, and the first and second 3-dimensional absorbent members, 2 and 3 respectively, contain superabsorbent 9, 10, and 11. The main absorbent 6, and the first and second 3-dimensional absorbent members, 2 and 3 respectively, are joined or secured to the transfer layer 4, when it is utilized, or to the lower surface of the liquid pervious top sheet 1. The main absorbent 6, and the first and second 3-dimensional absorbent members, 2 and 3 respectively, can be enclosed by the liquid pervious top sheet 1 and the liquid-impermeable back sheet 5. The first and second 3-dimensional absorbent members, 2 and 3 respectively, can flex and rise-up to fit up against the perineum area of a woman when she is wearing the sanitary napkin 7. The pressure created between the wearer's legs, her unique anatomy, and the size and shape of the sanitary napkin 7 will determine how the sanitary napkin 7 flexes.

The width of the sanitary napkin 7, located between the first and second ends, 30 and 20 respectively, will provide extra protection for they surround the first and second 3-dimensional absorbent members, 2 and 3 respectively. The liquid pervious top sheet 1 is joined or secured by the bond 47 to the underlying main absorbent 6 and to the first and second 3-dimensional absorbent members, 2 and 3 respectively. The sanitary napkin 7 includes a pair of wings, 15 and 21, which assist in securing the sanitary napkin 7 to an undergarment. Sometimes, the wings 15 and 21 are referred to as flaps or tabs.

While the invention has been described in conjunction with a single embodiment, it is to be understood that many alternatives, modifications and variations will be apparent to those skilled in the art in light of the foregoing description. Accordingly, this invention is intended to embrace all such alternatives, modifications and variations, which fall within the spirit and scope of the appended claims.

I claim:

1. A sanitary napkin having a body-facing surface, a garment-facing surface, a first end, a second end, and a pair of sides, said sanitary napkin having a longitudinal central axis and a transverse central axis, comprising:
   a) a liquid pervious top sheet having a body-facing surface;
   b) a liquid-impermeable back sheet having a garment-facing surface;
   c) a main absorbent positioned between said top sheet and said back sheet, said main absorbent containing a superabsorbent and said main absorbent having a top surface;
   d) a first 3-dimensional absorbent member secured to said top surface of said main absorbent and aligned along said longitudinal central axis and located between said first end of said sanitary napkin and said transverse central axis, and said first 3-dimensional absorbent member containing a superabsorbent;
   e) a second 3-dimensional absorbent member secured to said top surface of said main absorbent and aligned along said longitudinal central axis and located between said transverse central axis and said second end, and said second 3-dimensional absorbent member containing a superabsorbent,
   wherein the main absorbent, the first 3-dimensional member, and the second 3-dimensional member are joined together;
   f) a pair of flat top surface wings extending outward from said pair of sides of said sanitary napkin, each of said pair of flat top surface wings bifurcated by said transverse central axis, and each of said pair of flat top surface wings having a lower surface;
   g) a first garment adhesive secured to said garment facing surface of said sanitary napkin, said first garment adhesive releasably attaching said sanitary napkin to an interior surface of a crotch portion of an undergarment;
   h) two strips of garment adhesive, each strip of garment adhesive secured to one of said lower surfaces of each of said pair of flat top surface wings, said two strips of garment adhesive attaching to an exterior surface of a crotch portion folded underneath said undergarment; and
   i) removable peel strips covering a lower surface of said two strips of said garment adhesive,
   wherein said second 3-dimensional absorbent member has a pear shape with an apex, and said apex is positioned adjacent to said transverse central axis, wherein said apex has a height in a range of about 6 mm-8 mm, and
   wherein a transfer layer is positioned and joined between said top sheet, first and second 3-dimensional absorbent members and the main absorbent, said transfer layer covers 100% of said second 3-dimensional absorbent member, and said transfer layer covers only about 50% of said first 3-dimensional absorbent member.

2. The sanitary napkin of claim 1 wherein said first 3-dimensional absorbent member has an individual length of about 92 mm-100 mm.

3. The sanitary napkin of claim 1 wherein said second 3-dimensional absorbent member has an individual length about 52 mm.

4. The sanitary napkin of claim 1 wherein said first 3-dimensional absorbent member has a height of about 3 mm-15 mm.

5. The sanitary napkin of claim 1, wherein said main absorbent width is about 127 mm-145 mm.

6. The sanitary napkin of claim 1, further comprising a single release paper covering the first garment facing adhesive.

7. The sanitary napkin of claim 1, wherein said first garment adhesive width is about 76 mm-102 mm.

8. The absorbent member of claim 1, wherein said transfer layer has a weight of about 30 gsm-70 gsm.

9. The sanitary napkin of claim 1 wherein said first 3-dimensional absorbent member has a first end and a second end, said second end of first 3-dimensional absorbent member positioned closest to said first end of said sanitary napkin, said second 3-dimensional absorbent member has a first end and a second end, said second end of said second 3-dimensional absorbent member positioned closest to said second end of said sanitary napkin, the first end of said first 3-dimensional absorbent member, and the first end of said second 3-dimensional absorbent member being centrally arranged on the longitudinal central axis of said main absorbent.

10. The sanitary napkin of claim 1 wherein said first 3-dimensional absorbent member has a quadrilateral shape with a first end and a second end, and each of said first end and said second end having an arcuate shape, and wherein a thickness of the first 3-dimensional absorbent member and the second 3-dimensional absorbent member are each about 4 mm-6 mm.

* * * * *